United States Patent [19]
Whalon et al.

[11] Patent Number: 5,843,215
[45] Date of Patent: Dec. 1, 1998

[54] INSECT REPELLENT COATINGS

[75] Inventors: Mark E. Whalon, East Lansing, Mich.; Gene E. Malloy, Kenosha, Wis.

[73] Assignee: WARMM Sciences, LLC, Mason, Mich.

[21] Appl. No.: 835,378

[22] Filed: Apr. 7, 1997

[51] Int. Cl.$^6$ .......................... A01N 65/00; A01N 35/04
[52] U.S. Cl. ............................ 106/18.29; 106/15.05; 424/195.1; 424/405; 424/DIG. 10; 514/693; 514/699; 514/783; 514/919; 523/122
[58] Field of Search .................... 106/15.05, 18.29; 523/122; 424/195.1, DIG. 10, 405; 514/919, 693, 699, 783

[56] References Cited

U.S. PATENT DOCUMENTS

| | | | |
|---|---|---|---|
| 4,818,525 | 4/1989 | Kamada et al. | 424/403 |
| 4,990,381 | 2/1991 | Holzner | 428/35.3 |
| 4,997,650 | 3/1991 | Kamada et al. | 424/409 |
| 5,023,247 | 6/1991 | Boulanger et al. | 514/89 |
| 5,405,612 | 4/1995 | Locke et al. | 424/410 |
| 5,411,736 | 5/1995 | Locke et al. | 424/410 |
| 5,465,685 | 11/1995 | Dotolo et al. | 424/405 |
| 5,565,208 | 10/1996 | Vlasblom | 424/405 |
| 5,688,509 | 11/1997 | Radwan et al. | 424/195.1 |

FOREIGN PATENT DOCUMENTS

| | | | |
|---|---|---|---|
| 235584 | 9/1987 | European Pat. Off. | 106/18.31 |
| 54-000036 | 1/1979 | Japan | 106/15.05 |
| 59-172405 | 9/1984 | Japan | 106/15.05 |
| 59-227802 | 12/1984 | Japan | 106/15.05 |
| 3-250053 | 11/1991 | Japan | 106/15.05 |
| 999067 | 7/1965 | United Kingdom | 106/15.05 |

OTHER PUBLICATIONS

Smoley, C.K., "Everything Added to Food in the United States", US Food and Drug Administration, pp. 31, 32,36, 52,79,107,111 and 143, 1993.

Hackh's Chemical Dictionary, edited by Julius Grant, pp. 578, 579, 534 and 535, 1972.
Chemical Abstract No. 89:192516 which is an abstract of Japanese Patent Specification No. 53–075327 (Jul. 1978).
Chemical Abstract No. 98:84885 which is an abstract of Japanese Patent Specification No. 57–179105 (Nov. 1982).
Chemical Abstract No. 111:227252 which is an abstract of Japanese Patent Specification No. 62–000409 (Jan. 1987).
Chemical Abstract No. 115:130081 which is an abstract of Japanese Patent Specification No. 03–041010 (Feb. 1991).
Chemical Abstract No. 124:267542 which is an abstract of Japanese Patent Specification No. 08–033943 (Feb. 1996).
JAPIO Abstract No. JP401019004A which is an abstract of Japanese Patent Specification No. 01–019004 (Jan. 1989).
JAPIO Abstract No. JP403007210A which is an abstract of Japanese Patent Specification No. 03–007210 (Jan. 1991).
JAPIO Abstract No. JP404308510A which is an abstract of Japanese Patent Specification No. 04–308510 (Oct. 1992).
JAPIO Abstract No. JP406199618A which is an abstract of Japanese Patent Specification No. 06–199618 (Jul. 1994).
JAPIO Abstract No. JP406345613A which is an abstract of Japanese Patent Specification No. 06–345613 (Dec. 1994).
JAPIO Abstract No. JP407112907A which is an abstract of Japanese Patent Specification No. 07–112907 (May 1995).
JAPIO Abstract No. JP407215807A which is an abstract of Japanese Patent Specification No. 07–215807 (Aug. 1995).
JAPIO Abstract No. JP408059422A which is an abstract of Japanese Patent Specification No. 08–0595422 (Mar. 1996).

*Primary Examiner*—Anthony Green
*Attorney, Agent, or Firm*—Ian C. McLeod

[57] ABSTRACT

Coatings which comprise a water-based or water soluble resin and plant secondary compounds are described. The plant secondary compounds useful in the present invention consist of those compounds which have insecticidal characteristics. The coatings of the present invention have characteristics of insect repellence, antifeedance and oviposition deterrence.

16 Claims, No Drawings

INSECT REPELLENT COATINGS

BACKGROUND OF THE INVENTION

1. Field of the Invention

Flexible packaging materials including paper-board, plastic wraps and tin-foils are all used in packaging food-stuffs. Besides their obvious advantages, they suffer from a serious drawback in that unlike tins they are penetrated by insects leading to the contamination and putrefaction of the food stuff. The degree of insect penetration into a flexible package is relative to the type of flexible package, the environmental conditions around the package, the time of exposure to invading pests and the insect species involved [*Indian J. Ent.* 34(2); 94–101 (1972) "Resistance of Flexible Packaging Materials to Some Important Pests of Stored products" by Rao, Jacob and Mohan]. No single flexible packaging material has yet been found which is completely resistant to penetration by insect pests.

Stored product pests are a group of over 500 species of insects and mites. As a group, they are extremely varied in their size, survival strategy, life cycle, invasion behavior, acceptable diet items, and consequently, their stored product invasion capacity. For over 10,000 years man has attempted to devise various storage and packaging systems including the use of various pesticides like methyl bromide to protect against invasion, contamination and putrefaction by this army of pests. In the face of billions of dollars aimed at protecting stored products annually in the US, over 0.1% of all stored products are invaded, while in developing countries the invasion rate exceeds 30% in some countries.

In many instances, synthetic pesticides have been the only effective measure available for controlling stored product pests. However, synthetic pesticides have adverse effects on humans and the environment. (Entomological Society of America 1989, vol 82, no. 3, "Reproduction Retardant and Fumigant properties in Essential Oils Against Weevil in Stored Wheat"). Today, the use of synthetic pesticides to control stored product pests has been limited to commercial storage areas and has not been practical for consumer products packaging. The most effective chemical, methyl bromide, will be banned by the year 2000 because of its environmental (ozone depletion) impacts. Also, many stored product pests have developed the behavioral, metabolic and/or physiological means to escape the toxic effects of pesticides. This condition is termed 'pesticide resistance' and some stored product pests have developed resistance to such high levels that even a 3000 fold increase in application dosage will not kill 50% of them. In effect, some populations of stored product pests are unrestrained by either flexible packaging or pesticides.

Some plant secondary compounds including essential oils are thought to function as a natural defense for some plants against attacking insects, fungi and viruses. (Rosenthal, G. A. 1986, "The Chemical Defenses of Higher Plants" Sci. Am. 254; 76–81). These defensive chemicals possess many useful properties for insect control (Moore, P. D. 1986, "Toxins and Grazing Resistance" Nature 324; 410).

The present invention relates to print varnishes which contain certain natural plant secondary compounds. By natural we mean that these compounds are either extracted and purified directly from plants or are exact synthetic compounds to a plant secondary compound. Print varnishes are clear polymers used to coat paper products including flexible packaging. The plant secondary compounds utilized in the present invention are limited to those which have the characteristics of an insect or mite anti-feedant, repellent or oviposition arrestant. More particularly, the present invention relates to print varnishes useful in food packaging and which contain certain mixtures of these secondary plant compounds in combinations and amounts which impart reduced invasion by targeted stored product pest(s). Furthermore, the present invention utilizes natural plant secondary compounds that will ameliorate the selection for insecticide resistance by employing mixtures of plant secondary compounds at rates that will not kill pests, but will cause them to avoid the stored product, fail to recognize it as food or prevent oviposition. This feature is termed 'resistance management'.

2. Prior Art:

Certain plant secondary compounds, so called because they are often by-products of normal plant metabolism, from various plants have been found to have insecticidal characteristics. Studies conducted by G. Jilani, R. C. Saxena and B. P. Rueda as reported in *Entomological Society of America*, 1988. indicated that tumeric oil, sweetflag oil and neem oil, not only repel the red flour beetle (a cosmopolitan pest of stored cereals), but they also interfere with its normal reproduction and development. In this article, and other similar articles on the effectiveness of certain plant secondary compounds in repelling insects, the natural plant secondary compounds are applied directly to the food product to be protected, in this case, grain. In the present invention, plant secondary compounds are incorporated in coatings suitable for application to flexible packaging and other paper and plastic surfaces.

In U.S. Pat. No. 5,023,247, entitled "Insecticidal Coating Composition and Process for Making and Using It," a coating composition comprising a first phase containing a cross-linkable resin, a second phase containing water, and a third phase containing an insecticide dissolved in a solvent wherein the solvent is immiscible with the first phase and with water is described. These coating compositions kill insects even after exposure to weather for extended periods of time. The patented invention differs from the present invention in that the coatings of the patented invention are three phase coating systems in which the resin phase is unstable, whereas the coatings of the present invention are two phase emulsions wherein the active ingredients are suspended in the water phase. Also, the patented invention utilizes synthetic insecticides which kill insects while the present invention uses natural plant secondary compounds which repel, arrest feeding and/or arrest oviposition of insects and mites, thus avoiding pest invasion and, because of the unique combinations of secondary plant compounds employed, slow down genetic selection of the target pests which would become immune if a single compound were used or if toxic dosages of pesticides were used.

In U.S. Pat. No. 4,997,650, entitled "Insecticidal Resin Coating Film," an insecticidal resin coating film comprising a combination of an acrylonitrile and/or methacrylonitrile copolymer resin and an insecticidal component is described. The insecticidal component is kept on the surface of the coating film. In the present invention, the plant secondary compounds are disbursed throughout the coating film, thereby providing continued activity as some of the coating film is eroded over time. The coatings of the patented invention are applied directly to substrates which are infested with insects such as cockroaches, flies and termites. Also, the patented invention utilizes synthetic insecticides which kill insects while the present invention uses natural plant secondary compounds which repel, arrest feeding and/or arrest oviposition of insects and mites, thus avoiding pest invasion and, because of the unique combinations of secondary plant compounds employed, slow down genetic selection of the target pests which would become immune if a single compound were used or if toxic dosages of pesticides were used.

In U.S. Pat. No. 4,990,381, entitled "Multi-Layer Sandwich Sheet and packaging Using the Said Sheet", a multi-layer, laminated sandwich sheeting, comprising at least two layers superimposed and stuck together by welding or gluing is disclosed. One of the layers of patented invention comprises a material which is impervious to the active volatile agents of a perfuming or deodorizing composition, a flavoring agent (aroma) or an insecticidal or bacterial substance. The other layer is a polymeric material comprised of a polyolefin resin base or is made from a copolymer of polyamide and polyester, being premixed in a homogeneous manner with an active volatile agent. The insecticidal substances described as being useful in the patented invention are the synthetic insecticides: extract of pyrethrum, DDVP and Vaporthain. The patent does not disclose nor teach that plant secondary compounds have insect repellence, antifeedant activity or oviposition arrestant qualities useful as active ingredients when premixed with the polymeric material. Nor does it indicate that the insect control strategy will take advantage of mixtures of active ingredients or resistance management qualities.

In U.S. Pat. No. 4,818,525, entitled "Insecticidal Resin Coating Film", an insecticidal resin coating film which is formed mainly on a substrate so as to continuously and effectively kill and exterminate insects such as cockroaches, flies and termites which crawl on the coated substrate is described. The insecticides listed as being useful in the patented coating film are all synthetic insecticides which are included in amounts sufficient to kill insects. The naturally occurring insecticides of the present invention are included in the print varnishes of the present invention in amounts sufficient to repel, not kill, insects, thus avoiding the problem of "pest selection" wherein some of the insects become immune to the insecticide.

SUMMARY OF THE INVENTION

An object of the present invention is to provide print varnishes and other similar coatings which include certain plant secondary compounds and/or essential oils as ingredients. The plant secondary compounds and essential oils used in the present invention are selected based on their characteristics of insect repellence, antifeedance and oviposition deterrence, especially where combinations of these active ingredients exhibit synergistic effects of insect repellence, antifeedance and/or oviposition deterrence.

Bulk grain food, fruit, nut, dried fish and meat products are attacked by various insects and mites and their larvae. Even packaged grain food products are subject to such invasion. While stored in commercial warehouses, packaged grain food products are protected from insect invasion through fumigation with the use of insecticides such as methyl bromide. By far the most important stored-product pest control chemical, methyl bromide, is being phased out by industry in view of regulations by the U.S. Environmental Protection Agency which will prohibit the use of methyl bromide for such purposes by the year 2000. In the U.S. and throughout the world, stored product invasion rates are expected to escalate dramatically with the global banning of the use of methyl bromide as a fumigant and with the passage of legislation like the Food Quality and Protection Act which severely limits pesticide residues in food products. To further exacerbate pest invasion, other protectant insecticides have selected populations that are immune or "resistant" to these chemicals. In addition, insect protection ceases when packaged food products are stored on retail shelves or in homes.

Coatings, or print varnishes, of the present invention are valuable to the food industry for the following reasons:

1. The formulations (except for the inclusion of the secondary plant chemicals) and physical characteristics of the coatings of the present invention are essentially identical to existing print varnishes, therefore, these coatings can be applied to paperboard packaging without the need for additional equipment or new technology.
2. The multi-active ingredient formulas of the present invention act to synergistically enhance the antiovi-position and antecedant properties of the coatings at very low concentrations.
3. The low concentrations of active ingredients in the coatings minimize the risks of organoleptic detection in the food products.
4. Boxes protected by the dried films of the present invention do not lose their ability to protect the food products after the package is opened.
5. The inactive ingredients of the present coatings are approved by the U.S. Food and Drug Administration (FDA) for indirect food contact (21 CFR 175.105, 176.170 and 176.180).
6. The active ingredients of the present coatings have been approved by FDA as food additives (21 CFR 172.515, 172.520, 172.535(b), 182.10, 182.20, 182.40, 182.60 and 182.90).
7. The active ingredients of the present coatings acting together repel insects, prevent oviposition and/or act as antifeedants, thus not killing the pests, thereby delaying pest selection (pest resistance) or acquired immunities.
8. The active ingredients may be rotated and varied to provide future mixtures that can counteract pest resistance development.
9. Use of the present coatings on food packaging will contribute to methyl bromide alternatives, a critical development of national and international importance.

DETAILED DESCRIPTION OF THE INVENTION

Product Background

Print varnishes are clear coatings formulated for use in the printing industry. The formulations vary among manufacturers based on proprietary formulations, but all are based on common industry technology. Print varnish formulations are also adjusted depending upon the type of printing process for which they are to be used. Print varnishes may be formulated for use in gravure, sheetfed or flex printing processes. The print varnish formulations may also be adjusted for different curing processes such as, ultraviolet, infrared, electronic beam or hot air curing. Persons skilled in the manufacture of print varnishes will be able to produce coatings of the present invention for use in any of the above printing processes and curing processes.

The coatings of the present invention are clear acrylic resin coatings used to coat paper products. Some of the coated paper products are used on food packaging, such as cereal boxes, dried food boxes, dried fruit boxes and pet food products. All of the ingredients of these coatings are approved for indirect food contact by FDA. The active insect and mite behaviorally active ingredients added to the present coatings are derived from natural plant secondary compounds. The active ingredients are generally regarded as safe (GRAS) by FDA for use as food flavoring substances. They are listed in 21 CFR sections 172.515 and/or 182.60. Therefore, the coatings of the present invention avoid the use of toxic synthetic pesticides, and use only natural plant products.

The following is a list of some of the behaviorally active insecticidal ingredients of the coatings of the present invention. Also included in the list are the names of the plant secondary compounds and/or essential oils from which they are derived.

| Active ingredient | Derivative of |
|---|---|
| Cuminaldehyde | Eucalyptus, and other essential oils |
| Pinene | Oil of turpentine |
| Limonene | Various ethereal oils |
| Eucalyptol | Oil of eucalyptus |
| Perillaldehyde | Mandarin orange peel |
| Linalool | Cinnamon oil |
| Neem oil | Neem leaves and seeds |
| Turmerone | Turmeric |
| Asarone | Extract of sweetflag |
| Cinnamon oil | Cinnamon |

The effectiveness of the print varnishes of the present invention can be illustrated by explaining the life cycle of *plodia interpuntella*, the Indian meal moth, and its effect on packaged food products. The adult moth searches for places to lay its eggs which will provide nutrients for larvae which hatch from the eggs. The surfaces of packaged food products have microscopic openings which allow odors to be emitted from the boxes, thereby attracting moths. Even odor plumes of 10 ppm emanating from boxes are sufficient to stimulate oviposition in gravid Plodia females. Moths lay their eggs on the outside of the packages. When the eggs hatch, the larvae work their way into the packaging either by direct entry of by boring through the package material to eat the food product inside. After the pupa or cocoon (spin silk stage), the emerging adults leave the contaminated container and seek other mating and oviposition sites. It is the infestation of the packages by the larvae which has caused adverse economic and marketing effects on the packaged food industry.

There is a range of effects on insects caused by the natural plant secondary compound ingredients of the present invention. The effects are dependent upon the concentration of active ingredients, the mixture of compounds and the ambient environment. The effects range from: no effect at very low concentrations; antifeedant and repellency at higher concentrations; oviposition deterrence at still higher concentrations; and arrestant or analgesic characteristics at yet higher concentrations. The print varnishes of the present invention are formulated to contain active ingredients in amounts sufficient to only impart repellency, antifeedant and oviposition deterrent characteristics to the varnish. Varnishes with concentrations of active ingredients which are too low will have no effect on insect pests. If the concentration of active ingredients is too high, the coatings will have an analgesic effect on insect pests. They may become disoriented on the treated surface and lay all of their eggs on the surface, thereby increasing the amount of larvae which could enter the packaged food product. Therefore, the optimum amount of active ingredients useful in the present invention is that range of concentration which is sufficient to impart repellence, antifeedance and oviposition deterrence to the coated surface and less than that amount which will cause analgesic effects on the insects.

It was discovered through testing of the coatings of the present invention that the desirable range of active ingredients in the coatings should be from 0.03% to 0.3% by weight of the coating. Although the coatings may have some repellent qualities with active ingredient levels below 0.03%, because of the volatility of the plant secondary compounds, the coatings will lose their repellence in a short period of time with respect to the marketing and storage of packaged food products. Amounts greater than 0.3% may emit odors which are detectable by people. Although the odor may be pleasant to some, there is no market advantage in having food packaging which emits odors of various plant secondary compounds. In addition, at amounts greater than 0.3%, the plant secondary compounds may have an analgesic effect on some pest insects. In some cases, greater amounts of plant secondary compounds in the coatings may discolor or yellow clear print varnishes. All of these effects are not obvious to experts in the field, experts such as entomologists, organic chemists and natural product chemists.

Thirty-one naturally occurring essential oils of plant origin were studied under laboratory conditions for reproduction retardant, fumigant toxicity, and grain protection capability against the rice weevil, *Sitophilis oryzae* (L.). The results of the tests were reported by D. Singh, M. S. Siddiqui and S. Sharma in *Entomological Society of America*, vol. 82, no. 2, pp. 727–733, 1989. It was reported that the volatile oil obtained from *Pinus longifolia* Roxburgh significantly reduced the population of rice weevils, while in contrast, essential oils form *Callicarpa macrophylla* Vahl and *Zanthoxylum alatum* Roxburgh actually increased the insect population. It has been discovered that when the main components of *C. macrophylla* (limonene) and *Z. alatum* (linalool) are combined with certain other plant secondary compounds and included in print varnishes of the present invention, the paint varnishes are effective in repelling and oviposition deterrence of Indian meal moth adults, preventing feeding by larvae and other stored product pest so insects.

It was discovered through testing of coatings of the present invention that certain combinations of plant secondary compounds produced synergistic effects as pest insect repellents, antifeedants and oviposition deterrents. The optimum number of active ingredients in coatings appears to be three, which was not obvious prior to the present invention. By including three different active ingredients, coatings can be produced which repel several species of pest insects. Also, each active ingredient can be included in smaller quantities thereby reducing the odors which might be detected by humans. In some instances they may actually antagonize detection. The costs of the coatings may also be reduced by mixing more costly plant secondary compounds with less costly ones, while still maintaining the repellent, antifeedant and oviposition deterrent characteristics of the coating.

The paint varnishes described in the following examples are water based coatings. Water based paint varnishes have become the norm in the printing industry because, among other reasons, they have lower amounts of volatile organic compounds, lower toxicity and are more easily cleaned up. Never-the-less, the plant secondary compounds described herein can be added as insect repellents, antifeedants and oviposition deterrents to solvent based print varnishes too.

Since some of the plant secondary compounds which are included in the present invention are "oils" and the coatings to which they are added are water based products, special techniques are required for the proper dispersion of the compounds in the coatings. It has been discovered that the addition of alcohol to the plant secondary compounds prior to inclusion of the ingredients to the coating formulation and the use of high speed mills in the manufacture of the coatings successfully includes the active compounds in the coating. It is preferred that the alcohol used be of low molecular weight such as ethanol, n-butyl alcohol and isobutyl alcohol. It is also preferred that a minimum amount of alcohol (less than 5% by weight of the coating) be used in order to avoid altering the coating's application and performance qualities. This manufacturing strategy together with the inclusion of only small amounts (less than 0.3% by weight) of the plant secondary compounds results in behaviorally active coatings.

The following examples of print varnishes of the present invention are useful for gravure and sheetfed printing. The listed ingredients are mixed in high speed mills which are commonly used in print varnish and other coatings manufacture. Most of the ingredients are listed by their generic names. Specific formulas for the polymers, emulsions and other additives are typically proprietary to companies supplying such products to the coatings industry. Companies such as Morton International, S. C. Johnson, Sequa Chemicals, Goodyear and Rohm and Haas provide the listed ingredients under their own proprietary formulas. Companies in the business of manufacturing print varnishes are familiar with these and other sources of proprietary ingredients.

EXAMPLE 1

| Gravure Process Print Varnish | |
| --- | --- |
| Ingredient | Percent by Weight |
| Acrylic polymer | 65% |
| Styrene acrylic polymer | 15.0% |
| in water | 11.0% |
| Defoamer | 1.0% |
| Polyethylene wax emulsion | 5.0% |
| Silicone emulsion | 0.1% |
| Acrylic resin solution | 1.0% |
| Ethanol | 1.0% |
| Water | 0.6–0.8% |
| D-Limonene | 0.01–0.28% |
| Pinene | 0.01–0.28% |
| Cineole | 0.01–0.28% |

Wherein the total amount of D-Limonene, Pinene and Cineole does not exceed 0.3% by weight of the product and the total amount of these active ingredients.

EXAMPLE 2

| Gravure Process Print Varnish | |
| --- | --- |
| Ingredient | Percent by Weight |
| Acrylic polymer | 65.0% |
| Styrene acrylic polymer | 15.0% |
| in water | 11.0% |
| Defoamer | 1.0% |
| Polyethylene wax emulsion | 5.0% |
| Silicone emulsion | 0.1% |
| Acrylic resin solution | 1.0% |
| Ethanol | 1.0% |
| Water | 0.6–0.8% |
| Perillaldehyde | 0.01–0.28% |
| Cuminaldehyde | 0.01–0.28% |
| Linalool | 0.01–0.28% |

Wherein the total amount of Perillaldehyde, Cuminaldehyde and Linalool does not exceed 0.3% by weight of the product and the total amount of these active ingredients.

EXAMPLE 3

| Sheetfed Process Print Varnish | |
| --- | --- |
| Ingredient | Percent by Weight |
| Acrylic resin system | 17.0% |
| Styrene acrylic polymer | 20.0% |
| Butyl cellosolve | 3.0% |
| Acrylic resin | 45.0% |
| Surfactant/wetting agent | 3.0% |
| Defoamer | 0.5% |
| Ethyl alcohol | 3.0% |
| Polyethylene wax emulsion | 5.0% |
| Silicone emulsion | 0.1% |
| Water | 2.1–2.4% |
| D-Limonene | 0.01–0.28% |
| Pinene | 0.01–0.28% |
| Cineole | 0.01–0.28% |

Wherein the total amount of D-Limonene, Pinene and Cineole does not exceed 0.3% by weight of the product and the total amount of those active ingredients.

EXAMPLE 4

| Sheetfed Process Print Varnish | |
| --- | --- |
| Ingredient | Percent by Weight |
| Acrylic resin system | 17.0% |
| Styrene acrylic polymer | 20.0% |
| Butyl cellosolve | 3.0% |
| Acrylic Polymer | 45.0% |
| Surfactant/wetting agent | 3.0% |
| Defoamer | 0.5% |
| Ethyl alcohol | 3.0% |
| Polyethylene wax emulsion | 5.0% |
| Silicone emulsion | 0.1% |
| Water | 2.1–2.4% |
| Perillaldehyde | 0.01–0.28% |
| Cuminaldehyde | 0.01–0.28% |
| Linalool | 0.01–0.28% |

Wherein the total amount of Perillaldehyde, Cuminaldehyde and Linalool does not exceed 0.3% by weight of the product and the total amount of these ingredients.

Invasion Testing: Evaluation of Secondary Products in Real Time and Cupboard Condition.

Purpose:

To provide data that exhibits, as nearly as possible, the ability of the paint varnishes to protect stored food products in packages.

Test Period:

Boxes treated with print varnishes of the present invention are typically tested over an eight week period.

Methods and Materials:

Four environmental chambers are initially employed; three for the invasion test and a fourth to hold the "pulled" (removed from exposure to invading insects) sample boxes to prevent further invasion. The "pulled" boxes will be allowed to incubate so that the pest insects can develop to determine whether or not they have been invaded, and if they have been invaded, the invasion intensity. All chambers are maintained at 25°±2° C. throughout the study. The test boxes are allocated to shelves within chambers and to different chambers randomly to remove any operator bias in the experiment.

Moth and Beetle Release Density:

A content density of 5 gravid female moths and beetles per box is maintained in the test chambers throughout the invasion study. This means that the pest's invasion pressure will be constant throughout the test. This will mean that 150 moths and 150 beetles are introduced per treatment during the experiment, or a total of 1,050 moths and 1,050 beetles for the whole experiment. The adults have the capacity to produce approximately 630,000 moth larvae and 420,000 beetle larvae during the eight week test period.

Schedule of Pulls:

Groups of five boxes for each treatment are pulled from the test chambers on the following schedule: 1) initial inspection (0 days), 2) 1 week (7 days), 3) 2 weeks (14 days), 4) 4 weeks (28 days), 5) 6 weeks (42 days), and 6) 8 weeks (56 days). In addition, untreated controls are run in a separate chamber.

Number of Boxes:

A test for two types of coatings at three different concentrations of active ingredients will utilize one hundred and eighty treated boxes and thirty untreated control boxes.

Incubation and Box Inspection:

When the boxes are pulled from the test chambers they are sealed in a heavy gauge (9 mil) plastic bag, aerated, and placed into the holding chamber which is sealed to prevent further moth and beetle invasion. After an additional two week incubation period, the boxes are examined for pest invasion. Each box is opened, sieved to detect larvae, examined for adults, pupa and silk, and numerically ranked for invasion intensity.

Results:

Print varnishes of the present invention were found to repel Indian meal moths better than other repellents tested and far exceeded conventional board systems. Application rates as low as 0.01% significantly reduced Indian meal moth invasion when compared to conventional systems. Yet, even at the highest rates tested the varnishes were nontoxic to pests because the coatings exhibit a 0.1% lethal dose at rates 5 to 10 times higher than are applied in any of the formulations. The tested coatings elicited a behavior threshold response resulting in repellent, antifeedant and oviposition deterrent behavior over a wide range of concentrations. Tills result assures that the dry film of the coating will be effective as it weathers normally on cartons in storage and in marketing channels.

What we claim is:

1. A clear print varnish composition for application as a coating on paper products which comprises a water based or a water soluble and at least one plant compound, said plant compound being an insect repellent, antifeedant or oviposition deterrent and accepted for food use and is present in an amount of 0.01% to 0.3% by weight of the print varnish.

2. The print varnish composition according to claim 1 wherein the polymer is an acrylic polymer.

3. The print varnish composition according to claim 1 which contains more than one of the plant compounds which are selected from the group consisting of Cuminaldehyde, Pinene, Limonene, Eucalyptol, Perillaldehyde, Linalool, Turmeric and Cinnamon oil, and mixtures thereof, wherein each of the plant compounds included is in amounts ranging from 0.01% to 0.28% by weight and wherein all of the plant compounds together are 0.3% by weight or less of the print varnish.

4. A clear print varnish composition comprising the following ingredients in the percentage by weight amounts indicated:

| | |
|---|---|
| Acrylic polymer | 66% |
| Styrene acrylic polymer in water | 26% |
| Defoamer | 1.0% |
| polyethylene wax emulsion | 5.0% |
| Silicone emulsion | 0.1% |
| Ethanol | 1.0% |
| Water | 0.6–0.8% |
| D-Limonene | 0.01–0.28% |
| Pinene | 0.01–0.28% |
| Cineole | 0.01–0.28% | wherein the total amount of D-Limonene, Pinene and Cineole together does not exceed 0.3% by weight of the print varnish composition.

5. A clear print varnish composition comprising the following ingredients in the percentage by weight amounts indicated:

| | |
|---|---|
| Acrylic polymer | 66% |
| Styrene acrylic polymer in water | 26% |
| Defoamer | 1.0% |
| Polyethylene wax emulsion | 5.0% |
| Silicone emulsion | 0.1% |
| Ethanol | 1.0% |
| Water | 0.6–0.8% |
| Perillaldehyde | 0.01–0.28% |
| Cuminaldehyde | 0.01–0.28% |
| Linalool | 0.01–0.28% | wherein the total amount of Perillaldehyde, Cuminaldehyde and Linalool together does not exceed 0.3% by weight of the print varnish composition.

6. A clear print varnish composition comprising the following ingredients in the percent by weight amounts indicated:

| | |
|---|---|
| Acrylic polymer | 62% |
| Styrene acrylic polymer | 20% |
| Butyl cellosolve | 3.0% |
| Surfactant/wetting agent | 3.0% |
| Defoamer | 0.5% |
| Ethanol | 3.0% |
| Polyethylene wax emulsion | 5.0% |
| Silicone emulsion | 0.1% |
| Water | 2.1–2.4% |
| D-Limonene | 0.01–0.28% |
| Pinene | 0.01–0.28% |
| Cineole | 0.01–0.28% | wherein the total amount of D-Limonene, Pinene and Cineole together does not exceed 0.3% by weight of the print varnish composition.

7. A clear print varnish composition comprising the following ingredients in the percentage by weight amounts indicated:

| | |
|---|---|
| Acrylic polymer | 62% |
| Styrene acrylic polymer | 20% |
| Butyl cellosolve | 3.0% |
| Surfactant/wetting agent | 3.0% |
| Defoamer | 0.5% |
| Ethanol | 3.0% |
| Polyethylene wax emulsion | 5.0% |
| Silicone emulsion | 0.1% |
| Water | 2.1–2.4% |
| Perillaldeyde | 0.01–0.28% |

-continued

| | |
|---|---|
| Cuminaldehyde | 0.01–0.28% |
| Linalool | 0.01–0.28% | wherein the total amount of Perillaldehyde, Cuminaldehyde and Linalool together does not exceed 0.3% by weight of the print varnish composition.

8. A method of manufacturing a clear print varnish composition which comprises
   (a) mixing at least one plant compound which is insect repellent, antifeedant or oviposition deterrent and accepted for food use in an alcohol selected from the group consisting of ethanol, propyl alcohol and isopropyl alcohol, and;
   (b) mixing the alcohol and the at least one plant compound in a water-based or water soluble polymer which forms a coating on a container to be protected from the insect to produce the print varnish composition, wherein the at least one plant compound is present in a total amount of from 0.03% to 0.3% by weight of the print varnish composition.

9. A method of manufacturing an insect repellent, antifeedant or oviposition deterrent, clear print varnish composition which comprises
   (a) mixing more than one plant compound selected from the group consisting of Cuminaldehyde, Pinene, Limonene, Eucalyptol, Perillaldehyde, Linalool, Turmeric and Cinnamon oil and mixtures thereof, in amounts from 0.03% to 0.3% by weight of the print varnish and wherein all of the plant compounds together are 0.3% or less of the print varnish and an alcohol selected from the group consisting of ethanol, propyl alcohol and isopropyl alcohol to dissolve the plant compound; and
   (b) mixing the alcohol and plant compounds in a water-based or water soluble polymer which is a mixture of acrylic and styrene acrylic polymers to produce the print varnish.

10. A method for providing insect repellence, oviposition deterrent or antifeedant properties for a container which comprises applying a print varnish composition on the container which contains a polymer which forms a coating on the container and which coating contains at least one plant compound which provides the insect repellence, the oviposition deterrence or the antifeedant properties and is accented for food use in an amount from 0.01% to 0.3% by weight of the print varnish, wherein the total amount of the at least one plant compound is 0.3% or less by weight of the print varnish.

11. The method of claim 10 wherein the polymer is an acrylic polymer.

12. The method of claim 10 wherein more than one of the at least one plant compound are present in the print varnish and are selected from the group consisting of Cuminaldehyde, Pinene, Limonene, Eucalyptol, Perillaldehyde, Linalool, Turmeric, Cinnamon oil and mixtures thereof, wherein each of the plant compound included is in an amount from 0.01% to 0.28% by weight and wherein all of the plant compounds together are 0.3% or less by weight of the print varnish.

13. The method of claim 10 wherein the print varnish composition contains ingredients in the percentage by weight amounts indicated:

| | |
|---|---|
| Acrylic polymer | 66% |
| Styrene acrylic polymer in water | 26% |
| Defoamer | 1.0% |
| polyethylene wax emulsion | 5.0% |
| Silicone emulsion | 0.1% |
| Ethanol | 1.0% |
| Water | 0.6–0.8% |
| D-Limonene | 0.01–0.28% |
| Pinene | 0.01–0.28% |
| Cineole | 0.01–0.28% | wherein the total amount of D-Limonene, Pinene and Cineole does not exceed 0.3% by weight of the print varnish.

14. The method of claim 10 wherein the print varnish composition contains ingredients in the percentage by weight amounts indicated:

| | |
|---|---|
| Acrylic polymer | 66% |
| Styrene acrylic polymer in water | 26% |
| Defoamer | 1.0% |
| Polyethylene wax emulsion | 5.0% |
| Silicone emulsion | 0.1% |
| Ethanol | 1.0% |
| Water | 0.6–0.8% |
| Perillaldehyde | 0.01–0.28% |
| Cuminaldehyde | 0.01–0.28% |
| Linalool | 0.01–0.28% | wherein the total amount of Perillaldehyde, Cuminaldehyde and linalool does not exceed 0.3% by weight of the print varnish composition.

15. The method of claim 10 wherein the print varnish composition contains ingredients in the percent by weight amounts indicated:

| | |
|---|---|
| Acrylic polymer | 62% |
| Styrene acrylic polymer | 20% |
| Butyl cellosolve | 3.0% |
| Surfactant/wetting agent | 3.0% |
| Defoamer | 0.5% |
| Ethanol | 3.0% |
| Polyethylene wax emulsion | 5.0% |
| Silicone emulsion | 0.1% |
| Water | 2.1–2.4% |
| D-Limonene | 0.01–0.28% |
| Pinene | 0.01–0.28% |
| Cineole | 0.01–0.28% | wherein the total amount of D-Limonene, Pinene and Cineole does not exceed 0.3% by weight of the print varnish composition.

16. The method of claim 10 wherein the print varnish composition contains ingredients in the percentage by weight amounts indicated:

| | |
|---|---|
| Acrylic polymer | 62% |
| Styrene acrylic polymer | 20% |
| Butyl cellosolve | 3.0% |
| Surfactant/wetting agent | 3.0% |
| Defoamer | 0.5% |
| Ethanol | 3.0% |
| Polyethylene wax emulsion | 5.0% |
| Silicone emulsion | 0.1% |
| Water | 2.1–2.4% |
| Perillaldeyde | 0.01–0.28% |

-continued

| | |
|---|---|
| Cuminaldehyde | 0.01–0.28% |
| Linalool | 0.01–0.28% | wherein the total amount of Perillaldehyde, Cuminaldehyde and Linalool does not exceed 0.3% by weight of the print varnish composition.

* * * * *

UNITED STATES PATENT AND TRADEMARK OFFICE
CERTIFICATE OF CORRECTION

PATENT NO. : 5,843,215
DATED : December 1, 1998
INVENTOR(S) : Mark E. Whalon and Gene E. Malloy It is certified that error appears in the above-identified patent and that said Letters Patent is hereby corrected as shown below:

Column 6, line 36, delete "so".

Column 8, line 31, "Acrylic Polymer" should be --Acrylic Resin--.

Column 9, line 44, "Tills" should be --This--.

Column 11, line 50 (Claim 10), "accented" should be --accepted--.

Signed and Sealed this

Fourth Day of May, 1999

Attest:

Q. TODD DICKINSON

Attesting Officer

Acting Commissioner of Patents and Trademarks